United States Patent [19]
Hatfield et al.

[11] Patent Number: 5,840,032
[45] Date of Patent: Nov. 24, 1998

[54] METHOD AND APPARATUS FOR THREE-DIMENSIONAL ULTRASOUND IMAGING USING TRANSDUCER ARRAY HAVING UNIFORM ELEVATION BEAMWIDTH

[75] Inventors: William T. Hatfield, Schenectady, N.Y.; Todd Michael Tillman, West Milwaukee, Wis.; Douglas G. Wildes, Ballston Lake; Richard Y. Chiao, Clifton Park, both of N.Y.

[73] Assignee: General Electric Company, Milwaukee, Wis.

[21] Appl. No.: 852,264

[22] Filed: May 7, 1997

[51] Int. Cl.⁶ .................................................. A61B 8/00
[52] U.S. Cl. ............................................ 600/443; 128/916
[58] Field of Search .................................... 600/443, 437, 600/449; 128/916

[56] References Cited

U.S. PATENT DOCUMENTS

| | | | |
|---|---|---|---|
| 5,226,113 | 7/1993 | Cline et al. | 395/124 |
| 5,322,067 | 6/1994 | Prater et al. | 128/916 |
| 5,329,929 | 7/1994 | Sat et al. | 128/916 |
| 5,365,929 | 11/1994 | Peterson | 128/661.1 |
| 5,396,890 | 3/1998 | Weng | 600/443 |
| 5,474,073 | 12/1995 | Schwartz et al. | 128/661.1 |
| 5,485,842 | 1/1996 | Quistgaard | 128/660.07 |
| 5,582,173 | 12/1996 | Li | 128/660.07 |
| 5,655,535 | 8/1997 | Friemel et al. | 128/660.07 |

FOREIGN PATENT DOCUMENTS

WO 97/00482  1/1997  WIPO.

*Primary Examiner*—Marvin M. Lateel
*Assistant Examiner*—Maulin Patel
*Attorney, Agent, or Firm*—Dennis M. Flaherty; John H. Pilarski

[57] ABSTRACT

A method and an apparatus for three-dimensional imaging of ultrasound data by constructing projections of data from a volume of interest. An ultrasound scanner collects B-mode or color flow images in a cine memory, i.e., for a multiplicity of slices. A multi-row transducer array having a uniform elevation beamwidth is used to provide reduced slice thickness. In particular, the multi-row transducer array has a central row made up of elements having an area smaller than the combined area of the paired elements of two outermost rows The data from a respective region of interest for each of a multiplicity of stored slices is sent to a master controller, such data forming a volume of interest. The master controller performs an algorithm that projects the data in the volume of interest onto a plurality of rotated image planes using a ray-casting technique. The data for each projection is stored in a separate frame in the cine memory. These reconstructed frames are then displayed selectively by the system operator.

20 Claims, 5 Drawing Sheets

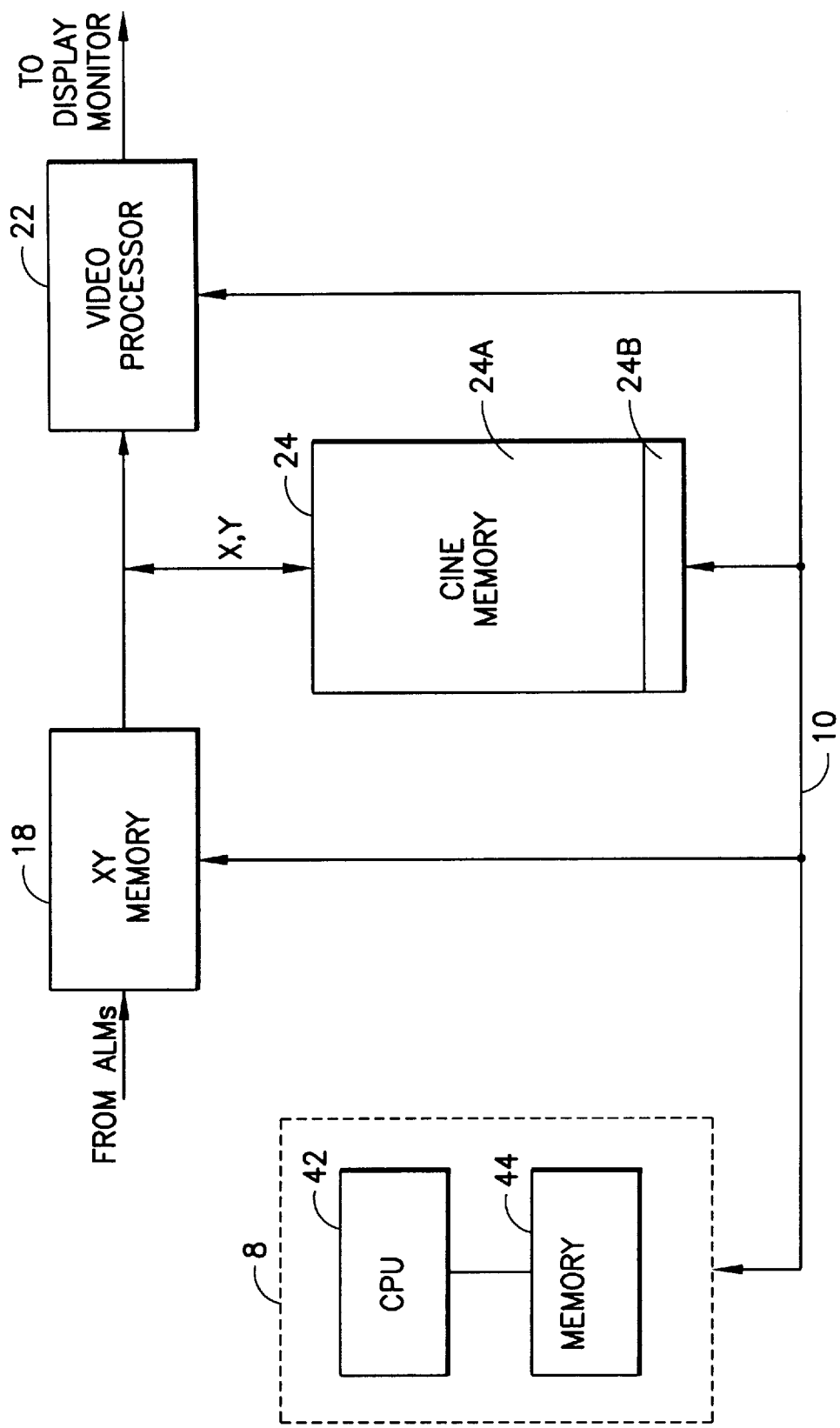

METHOD AND APPARATUS FOR THREE-DIMENSIONAL ULTRASOUND IMAGING USING TRANSDUCER ARRAY HAVING UNIFORM ELEVATION BEAMWIDTH

FIELD OF THE INVENTION

This invention generally relates to ultrasound imaging of the human anatomy for the purpose of medical diagnosis. In particular, the invention relates to apparatus for three-dimensional imaging of the human body and blood flowing therein by detection of reflected ultrasonic echoes reflected from the tissue or blood.

BACKGROUND OF THE INVENTION

The most common modes of diagnostic ultrasound imaging include B- and M-modes (used to image internal, physical structure), Doppler, and color flow (the latter two primarily used to image flow characteristics, such as in blood vessels). In conventional B-mode imaging, ultrasound scanners create images in which the brightness of a pixel is based on the intensity of the echo return. The color flow mode is typically used to detect the velocity of fluid flow toward/away from the transducer, and it essentially utilizes the same technique as is used in the Doppler mode. Whereas the Doppler mode displays velocity versus time for a single selected sample volume, color flow mode displays hundreds of adjacent sample volumes simultaneously, all superimposed on a B-mode image and color-coded to represent each sample volume's velocity.

Measurement of blood flow in the heart and vessels using the Doppler effect is well known. Whereas the amplitude of the reflected waves is employed to produce black and white images of the tissues, the frequency shift of backscattered waves may be used to measure the velocity of the backscatterers from tissue or blood. The backscattered frequency increases when blood flows toward the transducer and decreases when blood flows away from the transducer. Color flow images are produced by superimposing a color image of the velocity of moving material, such as blood, over the black and white anatomical image. The measured velocity of flow at each pixel determines its color.

The present invention is incorporated in an ultrasound imaging system consisting of four main subsystems: a beamformer 2 (see FIG. 1), a processor subsystem 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

The B-mode processor 4A converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels, heart cavities, etc. is shifted in proportion to the velocity of the blood cells: positively shifted for cells moving towards the transducer and negatively for those moving away. The color flow (CF) processor 4B is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. More specifically, the color flow processor produces velocity (8 bits), variance (turbulence) (4 bits) and power (8 bits) signals. The operator selects whether the velocity and variance or power are output to the scan converter 6. Ultimately, the output signal is input to a chrominance control lookup table which resides in the video processor 22.

The acoustic line memories 14A and 14B of the scan converter/display controller 6 respectively accept processed digital data from processors 4A and 4B and perform the coordinate transformation of the color flow and B-mode data from polar coordinate (R-θ) sector format or Cartesian coordinate linear array to appropriately scaled Cartesian coordinate display pixel data stored in X-Y display memory 18. In B mode, the intensity data is stored in X-Y display memory 18, each address storing three 8-bit intensity pixels. In color flow mode, the data is stored in memory as follows: intensity data (8 bits), velocity or power data (8 bits) and turbulence data (4 bits).

The scan converter 6 converts the acoustic image data from polar coordinate (R-θ) sector format or Cartesian coordinate linear array to appropriately scaled Cartesian coordinate display pixel data at the video rate. This scan-converted acoustic data is then output for display on display monitor 12. In the B mode, the monitor images the time-varying amplitude of the envelope of the signal as a grey scale, i.e., the brightness of a pixel is based on the intensity of the echo return. In the color flow mode, if movement is present, e.g., blood flowing in an artery, a Doppler shift in the return signal is produced proportional to the speed of movements. The display images the flow of blood, i.e., the Doppler shift using different colors, e.g., red for flow toward and blue for flow away from the transducer. In power Doppler imaging, the power contained in the returned Doppler signal is displayed.

Successive frames of color flow or B-mode data are stored in cine memory on a first-in, first out basis. Storage can be continuous or as a result of an external trigger event. The cine memory is like a circular image buffer that runs in the background, capturing image data that is displayed in real time to the user. When the user freezes the system, the user has the capability to view image data previously captured in cine memory. The graphics data for producing graphics overlays on the displayed image is generated and stored in the timeline/graphics processor and display memory 20. The video processor 22 multiplexes between the graphics data, image data, and timeline data to generate the final video output in a raster scan format on video monitor 12. Additionally it provides for various greyscale and color maps as well as combining the greyscale and color images.

Conventional ultrasound scanners create two-dimensional images of a "slice" through an area of the anatomy using a linear or curved phased-array transducer probe. FIGS. 5A and 5B shows a transducer array 100 comprising a plurality of separately driven transducer elements 102, each of which produces a burst of ultrasonic energy when energized by a pulsed waveform produced by a transmitter (not shown). The ultrasonic energy reflected back to transducer array 100 from the object under study is converted to an electrical signal by each receiving transducer element 102 and applied separately to the beamformer by a respective signal lead 108. In most conventional transducer arrays the elements 102 are arranged in a single row as seen in FIG. 5B, spaced at a fine pitch (one-half to one acoustic wavelength on center). In the elevation direction (perpendicular to the array axis and imaging plane), single-row transducer elements are large (tens of wavelengths) and beam formation is provided by a fixed-focus acoustic lens 110 (see FIG. 5A).

Conventional one-dimensional phased-array probes have excellent lateral and axial resolution, but their elevation performance is determined by a fixed aperture focused at a fixed range. The focal length of the lens is chosen to give maximum contrast resolution near the imaging range of greatest importance for the intended application of the probe. The elevation aperture is a tradeoff between contrast resolution and sensitivity near the lens focus (improved by a large aperture) and depth of field or contrast away from the focus (improved by a smaller aperture) The elevation aperture is typically $1/6$ to $1/3$ of the lens focus distance ($f/6$ to $f/3$), which gives good slice thickness (i.e., beamwidth in the plane perpendicular to the imaging plane, also referred to as "elevation beamwidth") and contrast resolution at the focus and a moderate depth of field. However, the near-field and far-field performance (elevation slice thickness and contrast resolution) of such a probe is significantly worse than the performance at the lens focus.

Referring to FIG. 2, the echo signals produced by each burst of ultrasonic energy reflect from objects located at successive ranges along the ultrasonic beam. The echo signals are sensed separately by each transducer element 102 and the magnitude of the echo signal at a particular point in time represents the amount of reflection occurring at a specific range. Due to the differences in the propagation paths between an ultrasound-scattering sample volume and each transducer element 102, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 46 receives the digitized echo signal from a respective transducer element 102.

To simultaneously sum the electrical signals produced by the echoes impinging on each transducer element 102, time delays are introduced into each separate beamformer channel 46 by a beamformer controller 104. The beam time delays for reception are the same delays as the transmission delays. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering the summer 106 are delayed so that when they are summed with delayed signals from each of the other beamformer channels 46, the summed signals indicate the magnitude and phase of the echo signal reflected from a sample volume located along the steered beam. A signal processor or detector 48 converts the received signal to pixel data. Scan converter 6 receives the pixel data from detector 48 and converts the data into the desired image for display on monitor 12.

Two-dimensional ultrasound images are often hard to interpret due to the inability of the observer to visualize the representation of the anatomy being scanned. However, if the ultrasound probe is swept over an area of interest and two-dimensional images are accumulated to form a three-dimensional volume, the anatomy is easier to visualize. The data may be manipulated in a number of ways, including volume or surface rendering. In addition, the data may be resampled and displayed in planes other than the ones in which the data was originally collected. This allows the user to obtain views of the anatomy that may not be possible given the anatomy and the inability to properly position the probe. The above techniques have been used to display ultrasound data with varying degrees of success. Typically, three-dimensional images of B-mode data and color flow velocity or power data are displayed separately.

One problem has been the limited range of elevational focus of the beam produced by a single-row, fixed single-focus transducer array. The source data slices used in the reconstruction of a three-dimensional image vary in thickness due to the nonuniform elevation beamwidth. Therefore, the reconstructed images successively degrade as projections or resampled images approach an angle perpendicular to the plane of acquisition. Thus there is a need to control the elevational focus of the ultrasound beam over a greater range, to obtain a much thinner slice of more uniform thickness, enabling improved three-dimensional imaging.

SUMMARY OF THE INVENTION

The present invention is a method and an apparatus for three-dimensional imaging by projecting ultrasound data acquired by scanning a volume of interest. The object volume is scanned using a multiplicity of parallel slices having a substantially uniform thickness. The ultrasound scanner collects B-mode or color flow mode images in a cine memory on a continuous basis or in response to an external trigger event, i.e., for a multiplicity of slices. The sample volume data from a respective region of interest for each slice is sent to a master controller, such data forming a volume of interest. The master controller performs an algorithm that projects the sample volume data in the volume of interest on a plurality of rotated image planes using a ray-casting technique. The sample volume data for each projection is stored, optionally with the portion of the last background frame lying outside the region of interest, in a separate frame in the cine memory. These reconstructed frames are then displayed selectively by the system operator.

A uniform elevation beamwidth is achieved through use of a multi-row transducer array. Various types of multi-row transducer arrays, including so-called "1.25D", "1.5D", and "2D" arrays, have been developed to improve upon the limited elevation performance of present single-row ("1D") arrays. As used herein, these terms have the following meanings: 1D) elevation aperture is fixed and focus is at a fixed range; 1.25D) elevation aperture is variable, but focusing remains static; 1.5D) elevation aperture, shading, and focusing are dynamically variable, but symmetric about the centerline of the array; and 2D) elevation geometry and performance are comparable to azimuth, with full electronic apodization, focusing and steering.

The three-dimensional ultrasound imaging system of the present invention employs a multi-row transducer array of the type which is not steerable in the elevation direction, namely, 1.25D and 1.5D arrays. The elevation aperture of a 1.25D probe increases with range, but the elevation focusing of that aperture is static and determined principally by a mechanical lens with a fixed focus (or foci). 1.25D probes can provide substantially better near- and far-field slice thickness performance than 1D probes, and require no additional system beam-former channels. 1.5D probes use additional beamformer channels to provide dynamic focusing and apodization in elevation. 1.5D probes can provide detail resolution comparable to, and contrast resolution substantially better than, 1.25D probes, particularly in the mid- and far-field.

In accordance with the preferred embodiment of the invention, the multi-row transducer array has one or more central rows made up of elements having an area smaller than the combined area of the paired elements of the outermost rows. This geometry provides excellent elevation performance (thinner and more uniform image slice, greater contrast resolution), especially in the very near field. Preferably, the array has five rows and a multi-focal lens, the combined area of each pair of elements in the outermost rows being greater than the area of each element of the central row and greater than the combined area of each pair of elements in the intermediate rows. In accordance with another variation, the array has only three rows and a bi-focal lens, the combined area of each pair of elements in the outer rows being greater than the area of each element of the central row. The array may also have more than five rows.

For 1.25D and 1.5D arrays with relatively few rows, a smaller central row will generally improve the nearfield resolution. If the multi-row transducer is used as a 1.25D array, then not only do small central row(s) improve the near field, but also large outer row(s), in conjunction with a multi-focus lens, provide improved elevation performance in the far field.

BRIEF DESCRIPTION OF THE DRAWINGS

FIG. 3 is a block diagram showing the means for reconstructing frames comprising successive volumetric projections of intensity and velocity or power pixel data in accordance with a preferred embodiment of the present invention.

FIG. 6—an array with Fresnel row widths, a single-focus lens and electrical connections for 1.5D beamforming; FIG. 7—an array with equal-area elements, a multi-focus lens and electrical connections for 1.25D beamforming; and FIG. 8—an array with relatively shorter (in the elevation direction) central rows and relatively taller outermost rows, a multi-focus lens and electrical connections for 1.25D beamforming.

DETAILED DESCRIPTION OF THE PREFERRED EMBODIMENTS

Figure 4:
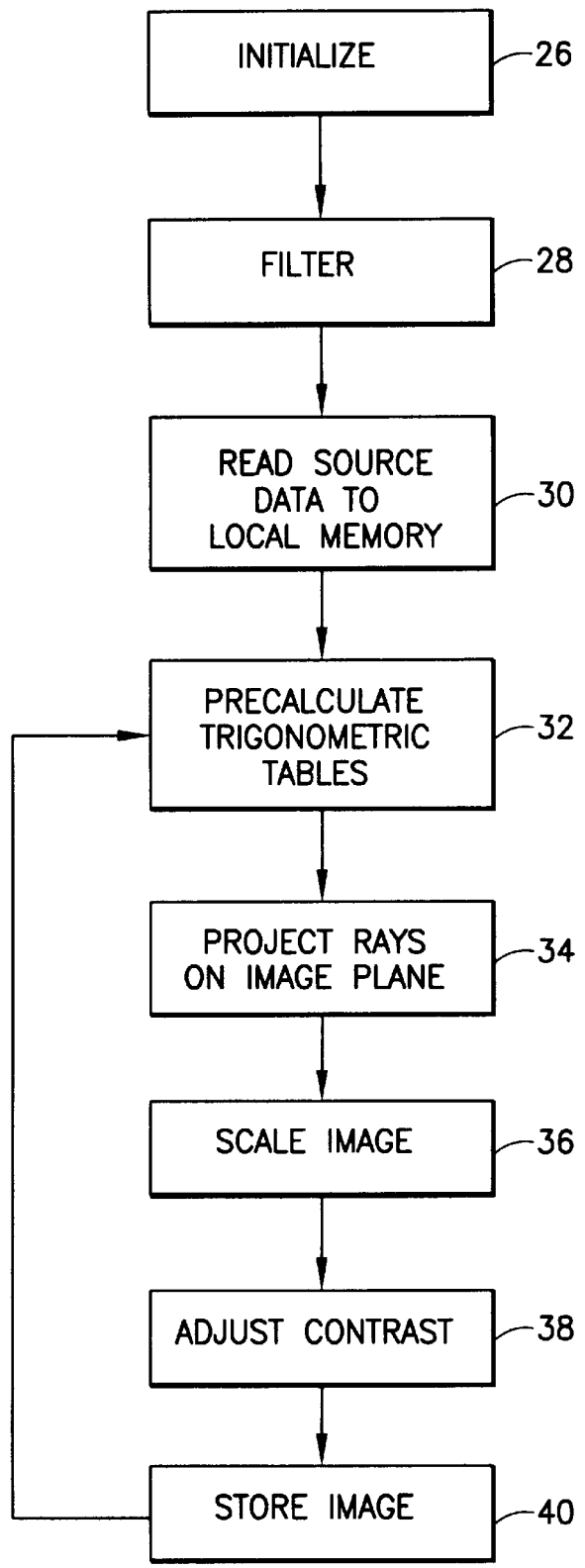
FIG. 4 is a flowchart showing the steps of an algorithm for reconstructing frames comprising successive volumetric projections of intensity and velocity or power pixel data in accordance with the preferred embodiment of the present invention.
Figure 5A:
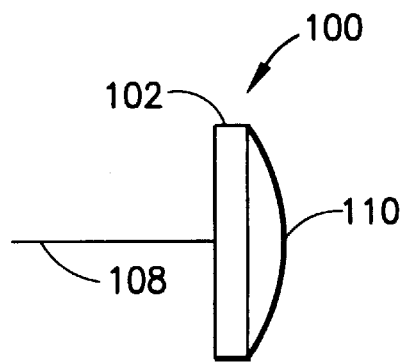
FIGS. 5A and 5B are elevation cross-sectional and frontal views, respectively, of a conventional 1D transducer array.
Figure 5B:
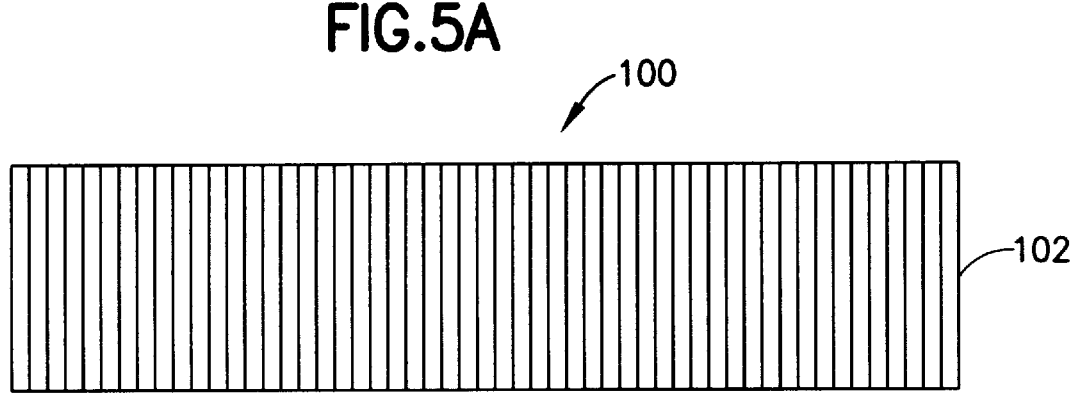

Referring to FIGS. 3 and 4, the method for projecting sample volume data into three-dimensional images in accordance with the invention will be disclosed. As seen in FIG. 3, the master controller 8 comprises a central processing unit (CPU) 42 and a random access memory 44. The CPU 42 has read only memory incorporated therein for storing routines used in transforming the acquired volume of sample volume data into a multiplicity of projection images taken at different angles. The CPU 42 controls the XY memory 18 and the cine memory 24 via the system control bus 10. In particular, CPU 42 controls the flow of data from XY memory 18 to video processor 22 and to cine memory 24, and from cine memory 24 to video processor 22 and to CPU 42 itself. Each frame of pixel data, representing one of a multiplicity of scans or slices through the object being examined, is stored in the XY memory 18 and in the next cycle is transmitted to video processor 22 and to cine memory 24. A stack of frames, representing the scanned object volume, is stored in section 24A of cine memory 24. During initialization (see step 26 in FIG. 3), the CPU 42 retrieves from cine memory section 24A only the pixel data corresponding to an object volume of interest. This is accomplished by retrieving only the pixel data in a region of interest from each stored frame acquired from any scan intersecting the object volume of interest. In other words, the pixel data corresponding to the region of interest from each one of a stack of successive frames forms a source data volume of interest.

Figure 1:
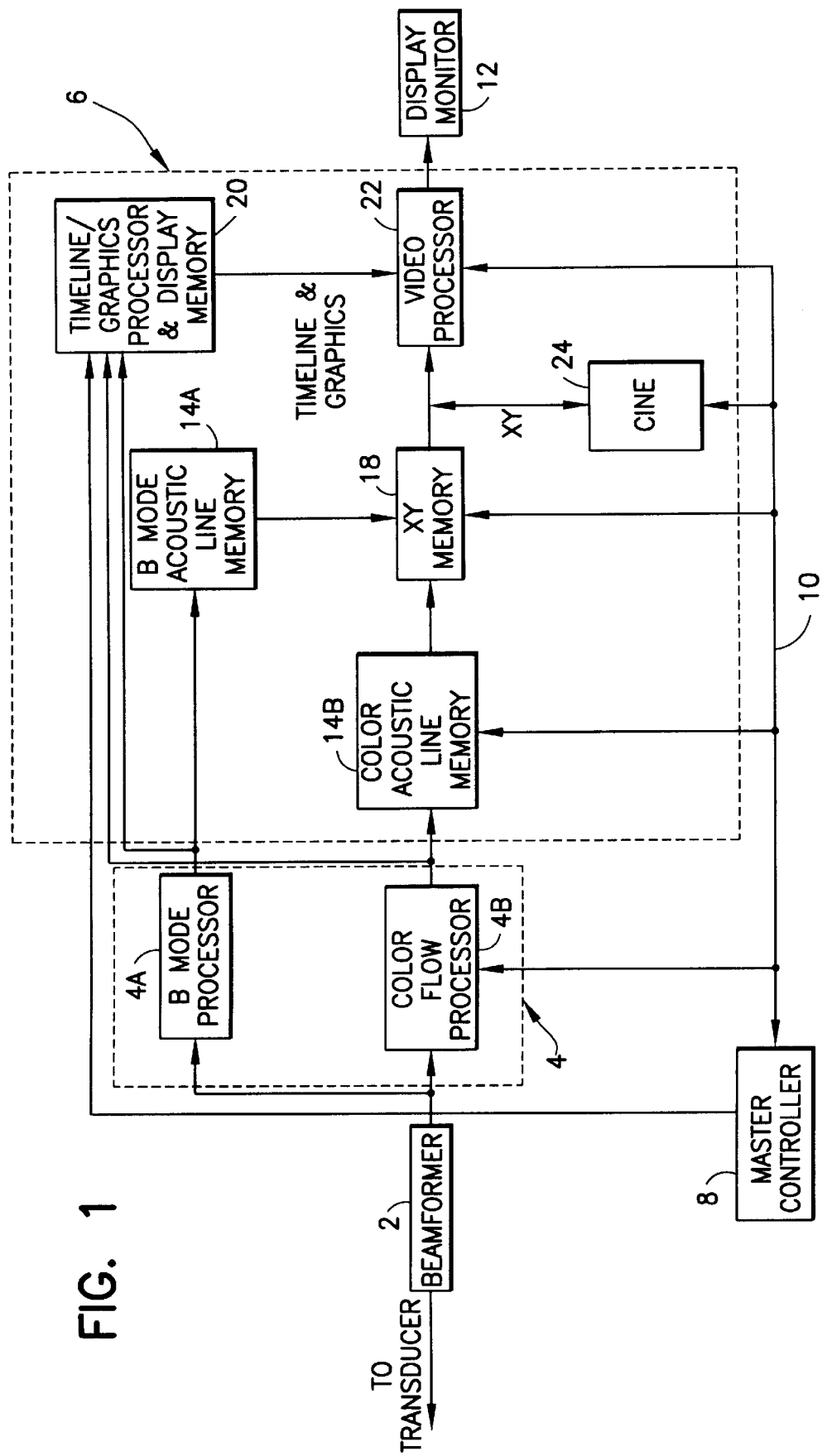
FIG. 1 is a block diagram showing the major functional subsystems within a real-time ultrasound imaging system.
Figure 2:
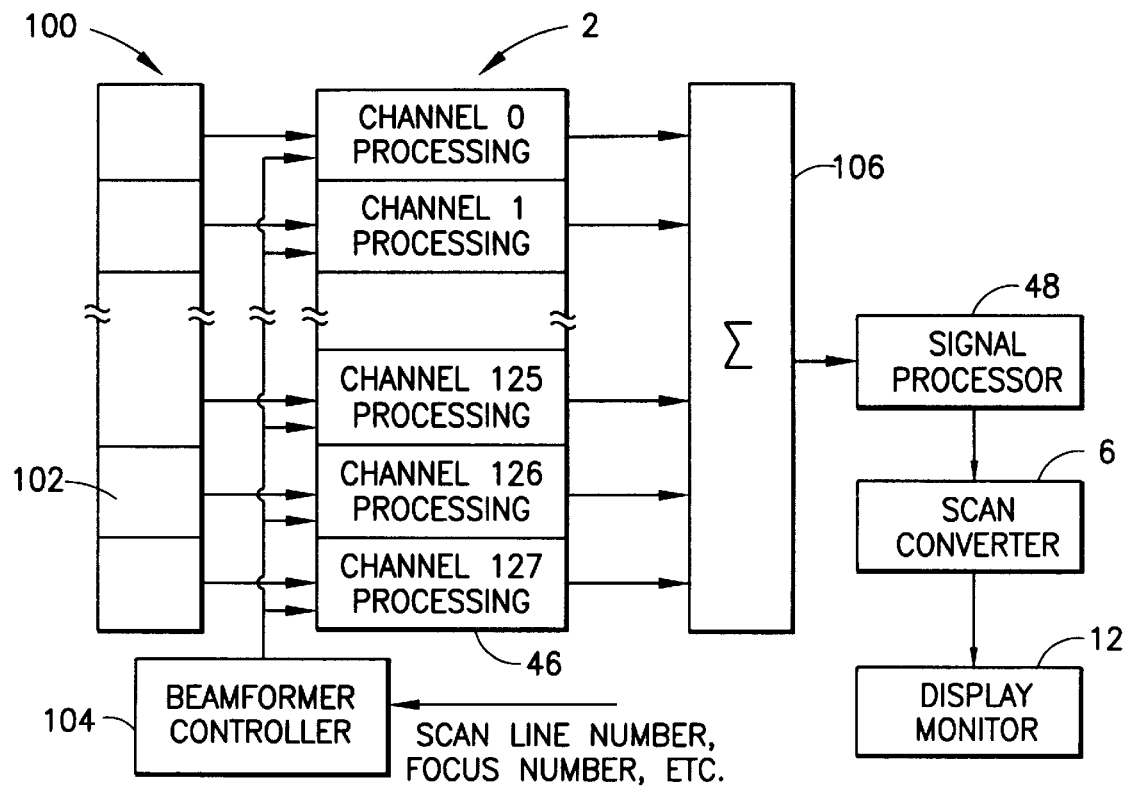
FIG. 2 is a block diagram of a typical 128-channel beamformer in a conventional ultrasound imaging system.

As seen in FIG. 4, the intensity data in the pixel data set corresponding to the object volume of interest is optionally filtered (step 28) prior to projection in order to smooth speckle noise and reduce artifacts. This prevents the loss of data due to speckle noise during projection. For example, blood vessels are less echogenic than the surrounding tissue. Therefore vessels can be imaged using minimum intensity projections. Alternatively, in the reverse video/minimum mode, the intensity data is inverted to make the vessels bright instead of dark. The vessels can then be imaged using maximum intensity projections. To prevent the selection of maximum intensities which are bright speckle as opposed to desired pixel data, a filter can be used to remove such bright speckle intensities prior to projection. The source data volume retrieved from the cine memory 24 (see FIG. 2) may be filtered by CPU 42 using, e.g., a 3×3 convolution filter having a 111 141 111 kernel, i.e., the central pixel of intensity data in each 3×3 pixel array in each slice or frame is replaced by an intensity value proportional to the sum of four times the value of the central pixel plus the sum of the values of the eight pixels surrounding that pixel. The filtered source data volume is then stored in memory 44 (step 30). In a similar manner, a convolution filter can be used to remove black holes in an image prior to minimum intensity projection.

Next the CPU 42 performs a series of transformations using the ray casting algorithm disclosed in U.S. Pat. No. 5,226,113, the contents of which are specifically incorporated by reference herein. The successive transformations represent maximum, minimum or averaged intensity, velocity or power projections made at angular increments, e.g., at 10° intervals, within a range of angles, e.g., +90° to −90°. However, the angular increment need not be 10°; nor is the invention limited to any particular range of angles.

In accordance with the ray casting technique employed in the present invention, volumetrically rendered projection images of a sample are displayed from any arbitrary viewing angle by scanning an object volume using an ultrasound transducer array having substantially uniform elevation beamwidth. The sample volume is scanned in such a manner as to create a series of stacked, contiguous slices, each of which contains the same number of object volume elements (voxels). Each voxel has a rectangular profile in the sheet plane (say, the X-Y plane); while the complementary sides may be of equal length, so that this profile may be square, the sheet thickness is generally greater than the length of either side.

Each object voxel is analyzed and the data value (intensity, velocity or power) thereof is placed in a corresponding data voxel of a data volume. The data volume is a simple cubic lattice, even though the thickness of each object slice and each object voxel face size (the size of the voxel in the X-Y plane) will generally not be the same.

In accordance with a known technique employed by CPU 42, an image of the object volume is projected (step 34 in FIG. 3) by ray casting toward an image plane from a lattice point in each data voxel. For convenience, the lattice point may, for example, be the data voxel vertex closest to the data volume origin. While all rays impinge upon some portion of the image plane, only those rays falling within the image plane pixel under consideration are allowed to contribute to the data for that image plane pixel. For a maximum pixel projection, each projected value is compared with the currently stored value and the larger of the two values is placed in storage for that pixel 60a. For a minimum pixel projection, the smaller of the two values is stored. As each voxel in the selected data volume is sequentially entered and projected toward the image plane, a data volume voxel is eventually projected along its associated ray and does not impinge within the desired pixel, so that its data value (e.g., intensity) is not compared to the data value presently stored for that pixel. The maximum data value for that pixel is now established, for that projection of the data at the particular three-dimensional angle of view. All data values are reset to zero when a new projection is to be taken. Thus, each of the image plane pixels is reset at the start of an image projection procedure, and all of the data volume voxels (in the entire space or in the selected portion, as set by the portion of the object volume selected) are individually and sequentially scanned. The data value in each data voxel is projected through an associated ray to impinge upon the image plane in one pixel thereof, with the maximum value in each pixel being compared between the present value of the ray-casted data volume voxel, to determine the larger thereof, which larger value is then stored as part of the maximum value image.

In accordance with another aspect of the foregoing technique, the data projection is scaled (step 36 in FIG. 3) and any anisotropy between the object volume and the image plane is removed by only a single set of calculations after back projection is complete. Because the object volume is a real volume while the data volume is an abstract concept, it is necessary to determine the amount of distortion of the data projection due to the presentation of the cubic data volume lattice at a different angle, in a first plane, than the angle at which an arbitrary viewing direction will be positioned with respect to both the object volume and data volume. The apparent dimensions of each voxel are going to change as the effective elevation angles change. If the aspect ratio (defined as the ratio of the actual slice thickness in the object volume to the actual pixel size in the same object volume) is not unity (i.e., is greater than unity), then the angles of elevation will be different, and the effective elevation angle in the data volume will be different than the actual elevation angle in the object volume. The data is then rotated in accordance with an object elevation angle. Thereafter, the projected data can be scaled to have the correct height (if rotation is about the horizontal axis) in the object volume, by multiplication of all projected data heights by an elevation scale factor. The elements of a 3×3 rotational matrix can be determined (as disclosed in U.S. Pat. No. 5,226,113), and these relationships are used to determine the data volume-to-image plane transformations. After the data is projected onto the image plane, the image is scaled to correct for the effect of the anisotropic object voxels. The factors in the rotational matrix can be precalculated (step 32 in FIG. 3) at the beginning of a projection and used for all rotation calculations.

In accordance with a further aspect of the invention, prior to display the scaled image plane data is mapped to achieve a desired brightness and contrast range (step 38 in FIG. 3).

The method shown in FIG. 3 can be applied to B-mode intensity data or to color flow velocity or power data for the data volume of interest retrieved from the cine memory. Each pixel in the projected image includes the transformed intensity data and the transformed velocity or power data derived by projection onto a given image plane. In addition, at the time when the cine memory was frozen by the operator, the CPU 42 optionally stores the last frame from the XY memory 18 at multiple successive addresses in section 24B of cine memory 24. The projected image data for the first projected view angle is written into the first address in cine memory section 24B, so that the projected image data in a region of interest is superimposed on the background frame. This process is repeated for each angular increment until all projected images are stored in cine memory section 24B, each projected image frame consisting of a region of interest containing transformed data and optionally a background perimeter surrounding the region of interest consisting of background frame data not overwritten by region-of-interest transformed data. The background image makes it clearer where each displayed projection is viewed from. The operator can then select any one of the projected images for display. In addition, the sequence of projected images can be replayed on the display monitor to depict the object volume as if it were rotating in front of the viewer.

In accordance with the present invention, improved elevation performance relative to that achieved in 1D arrays can be achieved by employing a multi-row transducer array configured as either a 1.25D array or a 1.5D array.

Figure 6:
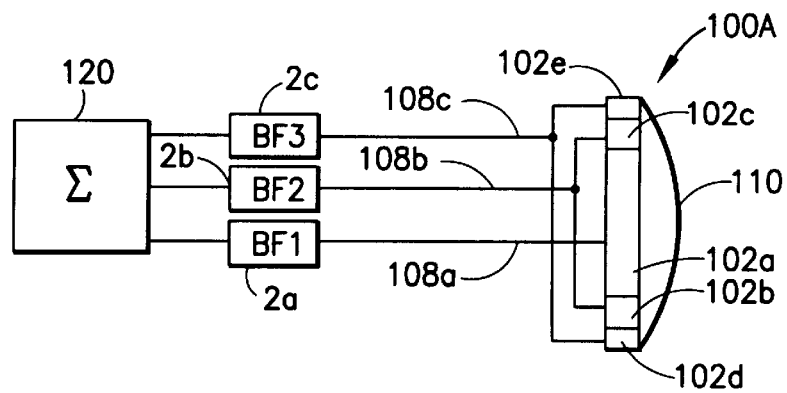
FIGS. 6–8 are elevation cross-sectional views of three multi-row transducer arrays which can be employed in the three-dimensional ultrasound imaging system of the present invention.

FIG. 6 shows a 1.5D array 10A with Fresnel row pitch and five rows 102a–102e of transducer elements, which can be used in the present invention to provide a more uniform elevation beamwidth than that obtainable with a 1D array. The ultrasound pulses are transmitted through a single-focus lens 110. If the centerline of the array is defined to be y=0 and the outer edge to be y=$y_{max}$, then the row edges are at distances $((1/3)^{1/2}, (2/3)^{1/2}, 1)y_{max}$ from the centerline. The signal leads 108a from the central row transducer elements are brought out for connection to a first set of beamforming channels 2a. The array elements in rows other than the central row are electrically connected in pairs, symmetric across the centerline. Signals leads 108b from each pair of intermediate row transducer elements are brought out for connection to a second set of beamforming channels 2b. Similarly, signals leads 108c from each pair of outermost row transducer elements are brought out for connection to a third set of beamforming channels 2c. The beamformer channels 2a–2c provide independent time delays, apodization and filtering for each transducer element or pair of elements in 1.5D array 10A. The outputs of the beamformer channels are combined in summer 120, analogous to summer 106 of the 1D beamformer shown in FIG. 2.

Figure 7:
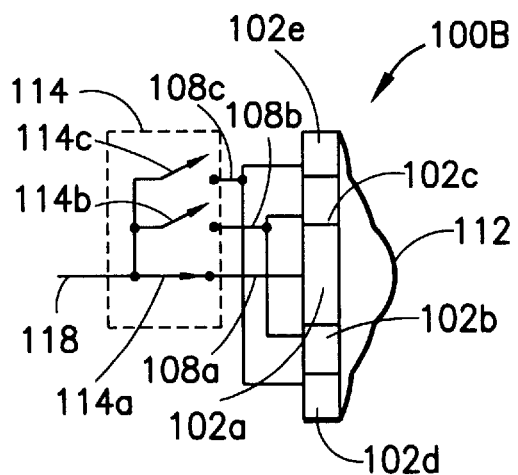

FIG. 7 shows a 1.25D array 10B with five rows 102a–102e of equal-area transducer elements, which can be used in the present invention to provide a more uniform elevation beamwidth than that obtainable with a 1D array. In this case, the ultrasound pulses are transmitted through a multi-focus lens 112. The row edges are at distances (1/3, 2/3, 1)$y_{max}$ from the array centerline. For each elevational column, the paired elements from the outer rows have a summed area which is the same as the area of each element of the central row. Thus, the pairs of elements in the outer rows have the same electrical impedance and acoustic sensitivity as that of the central row elements. The multi-focus lens improves the uniformity of the elevation beam profile by focusing the central row in the near field, where only the central row is active, and the outer rows in the far field, which is the only region where they are active.

In the 1.25D array shown in FIG. 7, a multiplicity of multiplexers 114 are respectively connected to a corresponding multiplicity of signal leads 118 (only one multiplexer and one signal lead are seen in FIG. 7). Each signal lead 118 is connected to a respective beamformer channel (not shown in FIG. 7). Each multiplexer 114 has three internal switches which multiplex signal leads 108a–108c to connect with signal lead 118. Each column of transducer elements is connected to a respective set of such signal leads: the central row element 102a being connected to signal lead 108a; the paired elements 102b, 102c of the intermediate rows being connected in to signal lead 108b; and the paired elements 102d, 102e of the outermost rows being connected in to signal lead 108c. In practice, the pairing of elements (i.e., connection of 102b to 102c and of 102d to 102e) are connected together within the probe head, whereas the multiplexers may be located within the probe head, at the console end of the probe cable or within the system console itself.

Because changing the state of the multiplexer switches generates noise, use of this probe typically requires three transmit-receive cycles per beam. With the multiplexer switches 114a for the center row of elements 102a closed and switches 114b and 114c open, the transmit delays are set to provide azimuthal focusing in the near field, and the near portion of the beam data is acquired. Next, switches 114a and 114b are closed, the transmit and receive delays are reconfigured, and the mid-field data is acquired using rows 102a, 102b and 102c. Finally, all the multiplexer switches are closed, the transmit and receive delays are reconfigured, and the far-field data is acquired using rows 102a–102e. Data from the three zones are spliced together in the imaging system, with care being taken to compensate for the change in sensitivity at the transition.

In accordance with the preferred embodiment of the invention, optimum elevation performance (minimum image slice thickness and maximum contrast resolution) is achieved with multi-row transducer arrays having a shorter (i.e., lesser height) central row and taller (i.e., greater height) outermost rows. The outermost rows are also taller in the elevation direction than any intermediate rows.

In the very near field, only the central row of the array is active and the elevation performance is determined by the height of the central row. For 1.25D and 1.5D arrays with relatively few rows, a smaller central row will generally improve the near-field resolution. The lower bound on the size of the central row elements is either the increasing loss associated with coupling a small, high-impedance element through a long cable to the beamformer electronics or the diminishing near-field distance ($Z \approx d/4\lambda$) and increasing divergence of the beam (half-angle $\theta \approx \sin^{-1}(\lambda/d)$) due to diffraction as the size of the element approaches an acoustic wavelength.

As the imaging depth increases from the near toward the far field, more of the rows of transducer elements become involved. To obtain uniform elevation performance over a maximum range, one would prefer to have the effective focal distance of the array increase as the active aperture increases. With a 1.25D array, all of the elevation focusing is provided by the acoustic lens. To increase the focal length as the aperture increases, a multi-focus lens is used.

Increasing the size of the outermost rows of the array relative to the inner rows gives greater weight in the far field of the image to the outer segments of the lens. This will further increase the effectiveness of the multi-focus lens and further improve the elevation depth of field and performance of the transducer.

With a 1.5D array and beamformer, some of the elevation focusing is achieved dynamically by adjusting electronic time delays in the beamformer. The beamformer also allows dynamic amplitude shading in elevation, which helps suppress sidelobes on the beam. These effects are hampered by and may outweigh the advantages of large outer rows and a multi-focus lens. Designing an array for optimum electronic focusing and shading in the far field leads to large central rows and small outer rows. The relevance of this invention to a 1.5D array design will depend on the importance of the near-field elevation performance of the probe relative to the far-field performance for the particular clinical application for which the probe is intended.

Many conventional multi-row transducer arrays have been designed with equal-area elements, so that all beamformer channels see the same electrical and acoustic impedance and all transducer elements have the same transmit and receive efficiency. However, most modern ultrasound imaging systems have transmit and receive apodization control (transmit amplitude and receive gain control) in their beamformers. This capability can be adapted or improved to compensate for variations in sensitivity, losses, and transmit/receive efficiency between the rows of a non-equal-area array. Therefore the non-uniform sensitivity and inverse apodization profile which might result from an uncompensated array which has small central and large outer rows should not be an issue when that array is connected to a properly designed imaging system.

Figure 8:
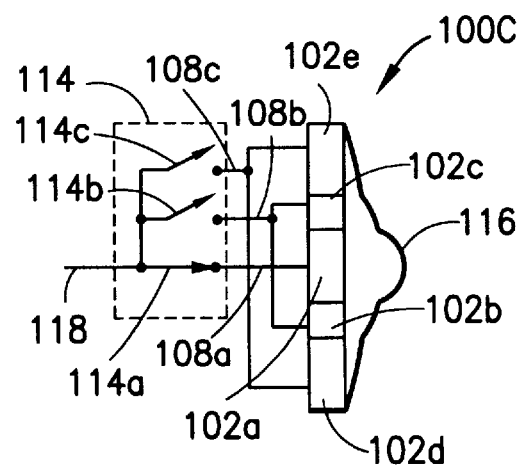

As one example of the application of the above array design principles, FIG. 8 shows a 5-row 1.25D array with a small central row 102a and large outermost rows 102d and 102e, which can be employed in the system of the present invention. The row edges are at distances (¼, ½, 1)$y_{max}$ from the array centerline. Thus, the paired elements of intermediate rows 102b and 102c have an area equal to the area of each element of central row 102a; and the paired elements of outermost rows 102d and 102e have an area equal to twice the area of each element of central row 102a. The ultrasound pulses are transmitted through a multi-focus lens 116 having lens foci of 35, 65 and 90 mm. The central section of lens 116, having a 35 mm focal length, focuses the ultrasound beams transmitted by central row 102a; the adjacent lens sections (65 mm focal length) focus the beams respectively transmitted by rows 102b and 102c; and the outermost lens sections (90 mm focal length) focus the beams respectively transmitted by outermost rows 102d and 102e. The connection and operation of the multiplexers 114 is the same as that previously disclosed with reference to FIG. 7.

The multi-focus lens 116 provides a delay function that is continuous across the elevation aperture but has a different curvature (focal length) for each row. Discontinuous delay functions are also possible, either by introducing discontinuities in the lens (which may cause diffraction artifacts) or by inserting static delay elements in the signal path between each row of elements and the multiplexer. The advantage of a multi-focus lens is that it substantially increases the depth of field, providing uniform resolution (−6 dB contour) and contrast (−20 dB contour) over essentially the entire imaging range of the probe. The disadvantage is that the sidelobes do not fall off quite as fast as those of a single-focus lens near its focal point.

The small-central-row design significantly improves the near-field performance of the 1.25D array. When combined with large outer rows and a multi-focus lens, the small-central-row design also provides modest improvement in the far field for the 1.25D array.

The row heights of the five-row 1.5D array shown in FIG. 6 can also be adjusted to provide outermost rows having greater height than the central row. In particular, the row edges can be the same as that disclosed for the 1.25D array shown in FIG. 8. This small-central-row design also significantly improves the near-field performance of the 1.5D array. However, for a 1.5D array, the small-central-row design causes broader sidelobes in the far field, so the choice between small-central-row and equal-area 1.5D arrays becomes a choice between near-field and far-field elevation performance.

Beam profile measurements and images confirm that multi-row arrays having small central rows have an elevation slice thickness which is remarkably uniform over the entire imaging range of the array, and have an imaging performance which is substantially better than that of comparable 1D probes.

In accordance with variants of the preferred embodiments shown in FIGS. 6 and 7, each transducer element in the central row 102a has a predetermined area, each pair of transducer elements in outer rows 102d and 102e have a first combined area greater than the predetermined area, and each pair of transducer elements in intermediate rows 102b and 102c have a second combined area not less than the predetermined area and not greater than the first combined area.

The 1.25D design in accordance with the preferred embodiment (see FIG. 7) provides near-field and far-field performance (slice thickness ≈ contrast resolution) which is substantially better than that of conventional 1D probes, and does not require any additional system beamformer channels. The increased elevation aperture and lens focal distance can contribute several dB to the probe's acoustic sensitivity in the far field; however, these gains may be offset by increased losses in the multiplexer and cable assembly.

In order to support dynamic elevation focusing, 1.5D arrays require many more beamforming channels and connections than 1.25D arrays. Elevational beam control for 1.25D arrays is accomplished only with a lens and a multiplexer. All elements within each elevational column of a 1.25D array are connected to the same beamforming channel and share the same electronic time delay and shading. In contrast 1.5D arrays use dynamic focusing and shading to control the elevational beam. With elevational symmetry (no steering), this requires an independent beamforming channel for each set of paired elevational elements.

Thus the distinction between simple and compound lenses is less important for 1.5D than for 1.25D. In a 1.25D array the lens is the only focusing mechanism and having a compound lens is crucial for maintaining good detail and contrast resolution over an extended range. In a 1.5D array the electronic focusing and apodization are sufficiently effective that a compound lens provides little advantage over a simple lens. The lens focus should be near the center of the range of interest.

In the case of 1.5D arrays, an elliptical active aperture can be used to reduce the number of channels used by the outermost rows and produce a beam profile which is superior to the beam profile of a rectangular aperture. In addition, synthetic aperture techniques and multiple transmit-receive cycles may be used to obtain 256- or 512-channel performance from a 128-channel imager.

The foregoing preferred embodiments have been disclosed for the purpose of illustration. Variations and modifications will be readily apparent to those skilled in the design of multi-row ultrasonic transducer arrays. All such variations and modifications are intended to be encompassed by the claims set forth hereinafter.

We claim:

1. A system for three-dimensional imaging of an ultrasound scattering medium in an object volume, comprising:

an ultrasound transducer array for transmitting ultrasound beams and detecting ultrasound echoes reflected in the object volume at predetermined sample volumes, said array comprising a first multiplicity of transducer elements arranged in a central row, a second multiplicity of transducer elements arranged in a first outer row, and a third multiplicity of transducer elements arranged in a second outer row, said central row being between said first and second outer rows, a first multiplicity of signal leads respectively connected to said first multiplicity of transducer elements, and a second multiplicity of signal leads respectively connected to said second and third multiplicities of transducer elements;

first means for focusing said first multiplicity of transducer elements on sample volumes in a near field;

second means for focusing said second and third multiplicities of transducer elements on sample volumes in a far field, said near field being located between said far field and said array;

first means for deriving a first set of pixel data from electrical pulses produced by said central row of transducer elements in response to detection of ultrasound transmitted by said central row and reflected by the scattering medium in near-field sample volumes;

second means for deriving a second set of pixel data from electrical pulses produced by said central row and said first and second outer rows of transducer elements in response to detection of ultrasound transmitted by said central row and said first and second outer rows and reflected by the scattering medium in far-field sample volumes;

means for forming vector data comprising pixel data from said first set and pixel data from said second set;

memory means for storing said vector data;

means for retrieving a set of vector data from said memory means corresponding to a volume of interest in the object volume;

means for projecting said vector data set onto a first image plane, thereby forming a projected data set representing a first projected image;

a display monitor; and means for displaying said first projected image on said display monitor.

2. The system as defined in claim 1, wherein said first focusing means comprise a first lens section of a multi-focus lens and said second focusing means comprise a second lens section of said multi-focus lens, said first lens section having a first focal length and said second lens section having a second focal length, said first lens section being acoustically coupled to said central row of transducer elements, and said second lens section being acoustically coupled to said first and second outer rows of transducer elements.

3. The system as defined in claim 2, wherein said second focal length is greater than said first focal length.

4. The system as defined in claim 1, further comprising:
a beamformer comprising a multiplicity of channels for forming transmit and receive beams;
a first multiplicity of switches for respectively connecting said first multiplicity of signal leads to said multiplicity of beamformer channels in a first switching state; and
a second multiplicity of switches for respectively connecting said second multiplicity of signal leads to said multiplicity of beamformer channels in a second switching state.

5. The system as defined in claim 1, wherein said first focusing means comprise a first set of beamformer channels for forming transmit and receive beams from electrical pulses carried by said first multiplicity of signal leads, and said second focusing means comprise a second set of beamformer channels for forming transmit and receive beams from electrical pulses carried by said second multiplicity of signal leads.

6. The system as defined in claim 1, further comprising:
means for projecting said vector data set onto a second image plane which is rotated relative to said first image plane, thereby forming a projected data set representing a second projected image; and
means for displaying said second projected image on said display monitor.

7. The system as defined in claim 1, wherein each of said first multiplicity of transducer elements has a predetermined area and each pair of said second and third multiplicities of transducer elements which are connected to a respective one of said second multiplicity of signal leads have a combined area greater than said predetermined area.

8. The system as defined in claim 1, further comprising a fourth multiplicity of transducer elements arranged in a first intermediate row, a fifth multiplicity of transducer elements arranged in a second intermediate row, and a third multiplicity of signal leads respectively connected to said fourth and fifth multiplicities of transducer elements, wherein said first intermediate row is between said central row and said first outer row, and said second intermediate row is between said central row and said second outer row.

9. The system as defined in claim 8, further comprising third means for focusing said fourth and fifth multiplicities of transducer elements on sample volumes in a mid-field, said mid-field being located between said near field and said far field.

10. A method for three-dimensional imaging of an ultrasound scattering medium in an object volume using a multi-row ultrasound transducer array, comprising the steps of:
focusing a central row of transducer elements of said array on sample volumes in a near field;
focusing first and second outer rows of transducer elements of said array on sample volumes in a far field, said near field being located between said far field and said array;
deriving a first set of pixel data from electrical pulses produced by said central row of transducer elements in response to detection of ultrasound transmitted by said central row and reflected by the scattering medium in near-field sample volumes;
deriving a second set of pixel data from electrical pulses produced by said central row and said first and second outer rows of transducer elements in response to detection of ultrasound transmitted by said central row and said first and second outer rows and reflected by the scattering medium in far-field sample volumes;
forming vector data comprising pixel data from said first set and pixel data from said second set;
storing said vector data;
retrieving a set of vector data from said memory means corresponding to a volume of interest in the object volume;
projecting said vector data set onto a first image plane, thereby forming a projected data set representing a first projected image; and
displaying said first projected image.

11. The method as defined in claim 10, further comprising the steps:
projecting said vector data set onto a second image plane which is rotated relative to said first image plane, thereby forming a projected data set representing a second projected image; and
displaying said second projected image.

12. A system for three-dimensional imaging of an ultrasound scattering medium in an object volume, comprising:
an ultrasound transducer array for transmitting ultrasound beams and detecting ultrasound echoes reflected in the object volume at predetermined sample volumes, said array comprising a first multiplicity of transducer elements arranged in a central row, a second multiplicity of transducer elements arranged in a first outer row, and a third multiplicity of transducer elements arranged in a second outer row, said central row being between said first and second outer rows, a first multiplicity of signal leads respectively connected to said first multiplicity of transducer elements, and a second multiplicity of signal leads respectively connected to said second and third multiplicities of transducer elements;
a beamformer comprising a multiplicity of channels for forming transmit and receive beams;
a first multiplicity of switches for respectively connecting said first multiplicity of signal leads to said multiplicity of beamformer channels in a first switching state;
a second multiplicity of switches for respectively connecting said second multiplicity of signal leads to said multiplicity of beamformer channels in a second switching state;
means for deriving pixel data from a multiplicity of receive beams formed by said beamformer channels, each pixel datum corresponding to a respective one of said predetermined sample volumes;
a memory for storing said pixel data;
means for retrieving a set of pixel data from said memory means corresponding to a volume of interest in the object volume;
means for projecting said pixel data set onto a first image plane, thereby forming a projected data set representing a first projected image;
a display monitor; and
means for displaying said first projected image on said display monitor.

13. The system as defined in claim 12, further comprising:
means for projecting said pixel data set onto a second image plane which is rotated relative to said first image plane, thereby forming a projected data set representing a second projected image; and
means for displaying said second projected image on said display monitor.

14. The system as defined in claim 12, wherein each of said first multiplicity of transducer elements has a predetermined area and each pair of said second and third multiplicities of transducer elements which are connected to a respective one of said second multiplicity of signal leads have a combined area greater than said predetermined area.

15. The system as defined in claim 12, further comprising a focusing lens comprising a first lens section having a first focal length and a second lens section having a second focal length greater than said first focal length, said first lens section being acoustically coupled to said central row of transducer elements, and said second lens section being acoustically coupled to said first and second outer rows of transducer elements.

16. The system as defined in claim 12, further comprising a fourth multiplicity of transducer elements arranged in a first intermediate row, a fifth multiplicity of transducer elements arranged in a second intermediate row, and a third multiplicity of signal leads respectively connected to said fourth and fifth multiplicities of transducer elements, wherein said first intermediate row is between said central row and said first outer row, and said second intermediate row is between said central row and said second outer row, and further comprising a third multiplicity of switches for respectively connecting said third multiplicity of signal leads to said multiplicity of beamformer channels in a third switching state.

17. The system as defined in claim 16, wherein each of said first multiplicity of transducer elements has a predetermined area and each pair of said second and third multiplicities of transducer elements which are connected to a respective one of said second multiplicity of signal leads have a first combined area greater than said predetermined area, and each pair of said fourth and fifth multiplicities of transducer elements which are connected to a respective one of said third multiplicity of signal leads have a second combined area not less than said predetermined area and not greater than said first combined area.

18. A system for three-dimensional imaging of ultrasound scattering matter in an object volume, comprising:

an ultrasound transducer array for transmitting ultrasound beams and detecting ultrasound echoes reflected from the object volume, said transducer array comprising a first multiplicity of transducer elements arranged in a central row, a second multiplicity of transducer elements arranged in a first outer row, and a third multiplicity of transducer elements arranged in a second outer row, said central row being between said first and second outer rows, a first multiplicity of signal leads respectively connected to said first multiplicity of transducer elements, and a second multiplicity of signal leads respectively connected to said second and third multiplicities of transducer elements;

first means for changing the azimuthal focusing of said transducer elements within each row to achieve changes in focal depth;

second means for changing the elevational focusing of said rows of transducer elements as a function of said focal depth;

means for coordinating said first and second changing means to acquire a source volume of pixel data derived from sample volumes in said object volume;

memory means for storing said source volume of pixel data;

means for retrieving a set of pixel data from said memory means corresponding to a volume of interest in the object volume;

means for projecting said pixel data set onto a first image plane, thereby forming a projected data set representing a first projected image;

a display monitor; and means for displaying said first projected image on said display monitor.

19. The system as defined in claim 18, wherein said second changing means controls said transducer array to have an elevation aperture which is increased with an increase in focal depth.

20. The system as defined in claim 18, further comprising:

means for projecting said pixel data set onto a second image plane which is rotated relative to said first image plane, thereby forming a projected data set representing a second projected image; and means for displaying said second projected image on said display monitor.

* * * * *